United States Patent
Atanasoska et al.

(10) Patent No.: US 9,414,821 B2
(45) Date of Patent: Aug. 16, 2016

(54) VASCULAR CLOSURE DEVICE WITH BIODEGRADABLE ANCHOR

(75) Inventors: Liliana Atanasoska, Edina, MN (US); David J. Sogard, Edina, MN (US); Robert W. Warner, Woodbury, MN (US); Michael Root, Lino Lakes, MN (US); Rajesh Radhakrishnan, Maple Grove, MN (US); Mourad Rahi, Roseville, MN (US); Scott R. Smith, Chaska, MN (US); Jan Weber, Maastricht (NL); Eric Petersen, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1356 days.

(21) Appl. No.: 12/841,895

(22) Filed: Jul. 22, 2010

(65) Prior Publication Data

US 2012/0022585 A1 Jan. 26, 2012

(51) Int. Cl.
*A61B 17/08* (2006.01)
*A61B 17/00* (2006.01)

(52) U.S. Cl.
CPC ... *A61B 17/0057* (2013.01); *A61B 2017/00004* (2013.01); *A61B 2017/00411* (2013.01); *A61B 2017/00654* (2013.01); *A61B 2017/00659* (2013.01)

(58) Field of Classification Search
CPC .............. A61B 17/0057; A61B 2017/00004; A61B 2017/00411; A61B 2017/00659
USPC .......... 424/422, 423, 426, 444; 606/213, 215, 606/216; 604/20, 285, 286; 623/1.38; 128/887
See application file for complete search history.

(56) References Cited

U.S. PATENT DOCUMENTS

| | | |
|---|---|---|
| 5,360,440 A | 11/1994 | Andersen |
| 5,490,859 A | 2/1996 | Mische et al. |
| 5,501,694 A | 3/1996 | Ressemann et al. |
| 5,540,707 A | 7/1996 | Ressemann et al. |
| 5,836,868 A | 11/1998 | Ressemann et al. |
| 5,897,567 A | 4/1999 | Ressemann et al. |
| 6,287,332 B1 | 9/2001 | Bolz et al. |
| 6,306,243 B1 | 10/2001 | Clark et al. |
| 6,663,650 B2 | 12/2003 | Sepetka et al. |
| 6,824,545 B2 | 11/2004 | Sepetka et al. |
| 7,285,126 B2 | 10/2007 | Sepetka et al. |
| 7,527,637 B2 | 5/2009 | Sater et al. |
| 7,534,252 B2 | 5/2009 | Sepetka et al. |
| 7,686,825 B2 | 3/2010 | Hauser et al. |
| 2004/0073243 A1 | 4/2004 | Sepetka et al. |
| 2004/0098025 A1 | 5/2004 | Sepetka et al. |

(Continued)

FOREIGN PATENT DOCUMENTS

| | | |
|---|---|---|
| WO | 02053202 A1 | 7/2002 |
| WO | 2009108750 A1 | 9/2009 |

OTHER PUBLICATIONS

Loffler, Jorg F. et al., "MgZnCa Glasses without Clinically Observable Hydrogen Evolution for Biodegradable Inputs," Nature Materials, 3:887-891 (Nov. 2009). On-line at www.nature.com/naturematerials.

*Primary Examiner* — Robert Lynch
(74) *Attorney, Agent, or Firm* — Seager, Tufte & Wickhem LLP

(57) ABSTRACT

This disclosure pertains to controllably bioabsorbable devices, particularly anchors for vascular closure plugs and to methods of use thereof.

20 Claims, 3 Drawing Sheets

(56) References Cited

U.S. PATENT DOCUMENTS

| | | |
|---|---|---|
| 2005/0049619 A1 | 3/2005 | Sepetka et al. |
| 2005/0220837 A1 | 10/2005 | Disegi et al. |
| 2005/0261760 A1 | 11/2005 | Weber |
| 2005/0267560 A1 | 12/2005 | Bates |
| 2006/0052825 A1 | 3/2006 | Ransick et al. |
| 2006/0184092 A1* | 8/2006 | Atanasoska et al. ............ 604/20 |
| 2006/0195137 A1 | 8/2006 | Sepetka et al. |
| 2007/0141106 A1* | 6/2007 | Bonutti et al. ................ 424/423 |
| 2007/0208371 A1 | 9/2007 | French et al. |
| 2007/0219576 A1 | 9/2007 | Cangialosi |
| 2007/0219623 A1 | 9/2007 | Palmaz |
| 2007/0270942 A1 | 11/2007 | Thomas |
| 2008/0071348 A1* | 3/2008 | Boismier et al. ............. 623/1.15 |
| 2008/0071350 A1 | 3/2008 | Stinson |
| 2008/0109031 A1 | 5/2008 | Sepetka et al. |
| 2008/0188876 A1 | 8/2008 | Sepetka et al. |
| 2008/0200600 A1 | 8/2008 | Schomaker et al. |
| 2008/0215077 A1 | 9/2008 | Sepetka et al. |
| 2008/0234706 A1 | 9/2008 | Sepetka et al. |
| 2008/0262532 A1 | 10/2008 | Martin |
| 2008/0305341 A1* | 12/2008 | Plieth et al. ................... 428/419 |
| 2009/0069828 A1 | 3/2009 | Martin et al. |
| 2009/0299393 A1 | 12/2009 | Martin et al. |

* cited by examiner

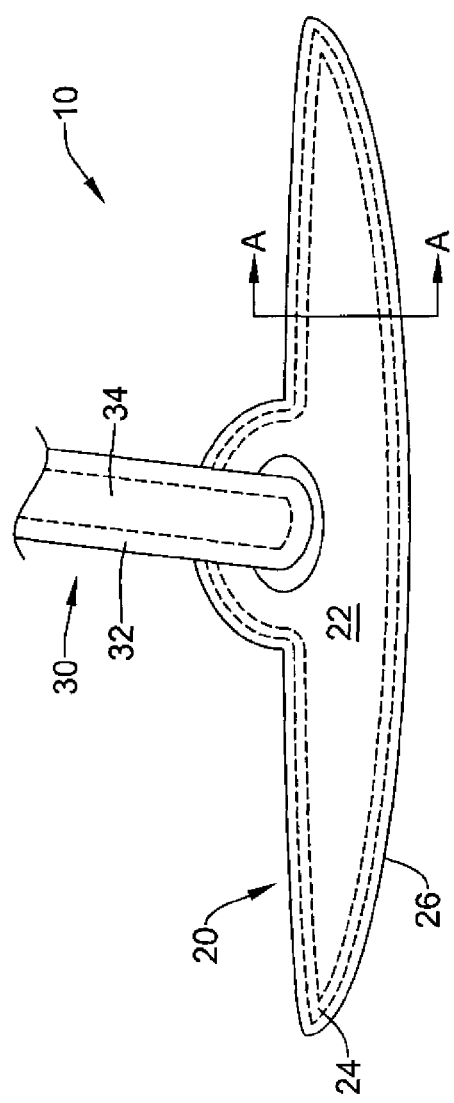
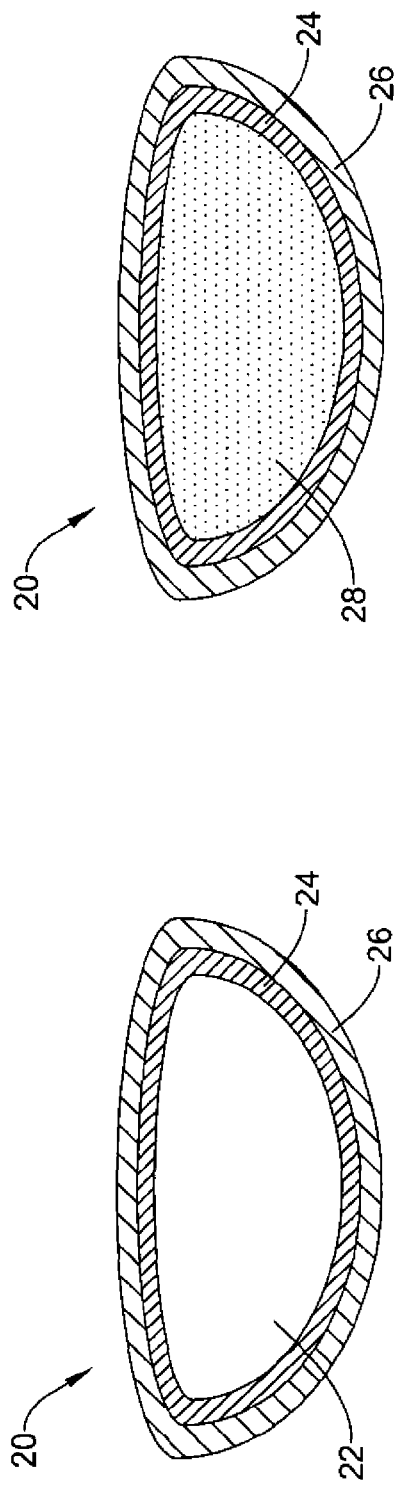

VASCULAR CLOSURE DEVICE WITH BIODEGRADABLE ANCHOR

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

The non-invasive medical procedures identified above typically gain access to the vasculature through an opening formed in the femoral artery. For obvious reasons, once the procedure is completed the opening in the femoral artery will need to be closed. This may include applying direct pressure at the wound site. Alternatively, a device may be used to assist in the closing of the artery.

A wide variety of medical devices have been developed for medical uses, for example, in non-invasive medical procedures. Some of these devices include devices for closing an opening in a body lumen such as the femoral artery. Closure devices for closing an opening in a body lumen may include a plug such as a collagen sponge, a dissolving anchor, and a suture coupling the plug to the anchor. The dissolving anchor may be configured to dissolve in the body lumen within about 60 to 90 days or less. At least a portion of the dissolving anchor may be disposed within the body lumen. Although the anchor may have served the purpose of positioning and securing the plug adjacent to the vessel within the first few hours following surgery, such anchors are frequently designed to dissolve more slowly to ensure that they continue to function during the post operative period and to minimize the likelihood that a significant piece of the anchor may be released into the blood stream during the dissolution process. Other difficulties may arise if it becomes necessary to re-enter the wound site before the anchor has fully dissolved.

Accordingly, it would be desirable to provide an anchor which dissolves rapidly and controllably while positioned within the vessel.

SUMMARY

This disclosure pertains to controllably bioabsorbable devices, particularly anchors for vascular closure plugs. In some embodiments, the anchors provide a bioabsorbable anchor for a vascular closure device comprising a magnesium anchor element, a biodegradable polymer coating the magnesium anchor element, a biodegradable electroactive polymer, and a conductive element connected to the magnesium anchor.

Advantageously, the bioabsorbable anchor may comprise a heteropolyacid. In addition, the anchors may include a source of electric current connected to the magnesium anchor by the conductive element. The source of electric current may be an external battery or may be provided by an electrochemical reaction within the body.

The controllably bioabsorbable anchors described herein may be disposed in a vessel to be sealed by devices employed in the art for that purpose. Once the anchor is within the vessel with the conductive element extending through the puncture site in the wall of the vessel, tension may be applied to the conductive element to seat the anchor against the interior vessel wall at the puncture site. With the anchor properly in place, a biodegradable hemostatic plug may be positioned adjacent to the exterior vessel wall opposite the anchor and allowed to swell or otherwise seal the wound tract. An electric current may then be passed through the conductive element to the anchor to cause the anchor to dissolve at a rate different from the rate at which the anchor would dissolve in the absence of an electric current.

BRIEF DESCRIPTION OF DRAWINGS

FIG. 1 illustrates an embodiment of the invention.

FIG. 1A illustrates a cross-sectional view of the embodiment of FIG. 1.

FIG. 1B illustrates a cross-sectional view of a variation of the embodiment of FIG. 1.

DETAILED DESCRIPTION

Figure 2:
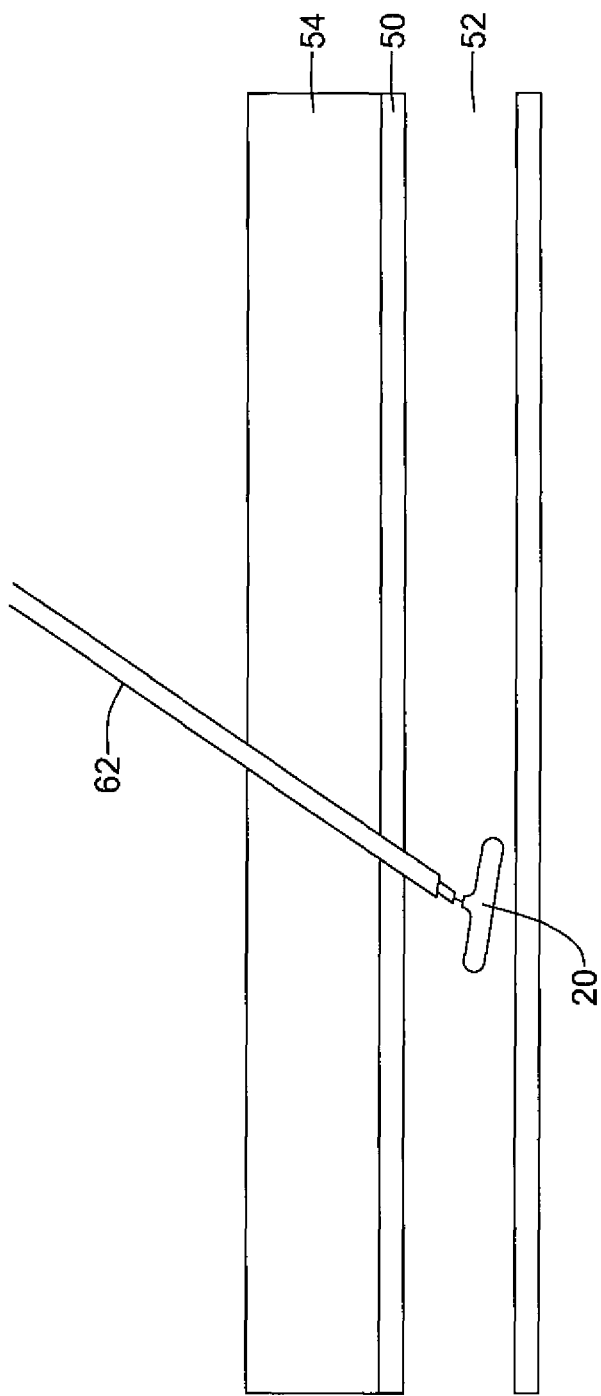
FIG. 2 illustrates an embodiment of the disclosure initially deployed in a punctured blood vessel.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments whether or not explicitly described.

Figure 3:
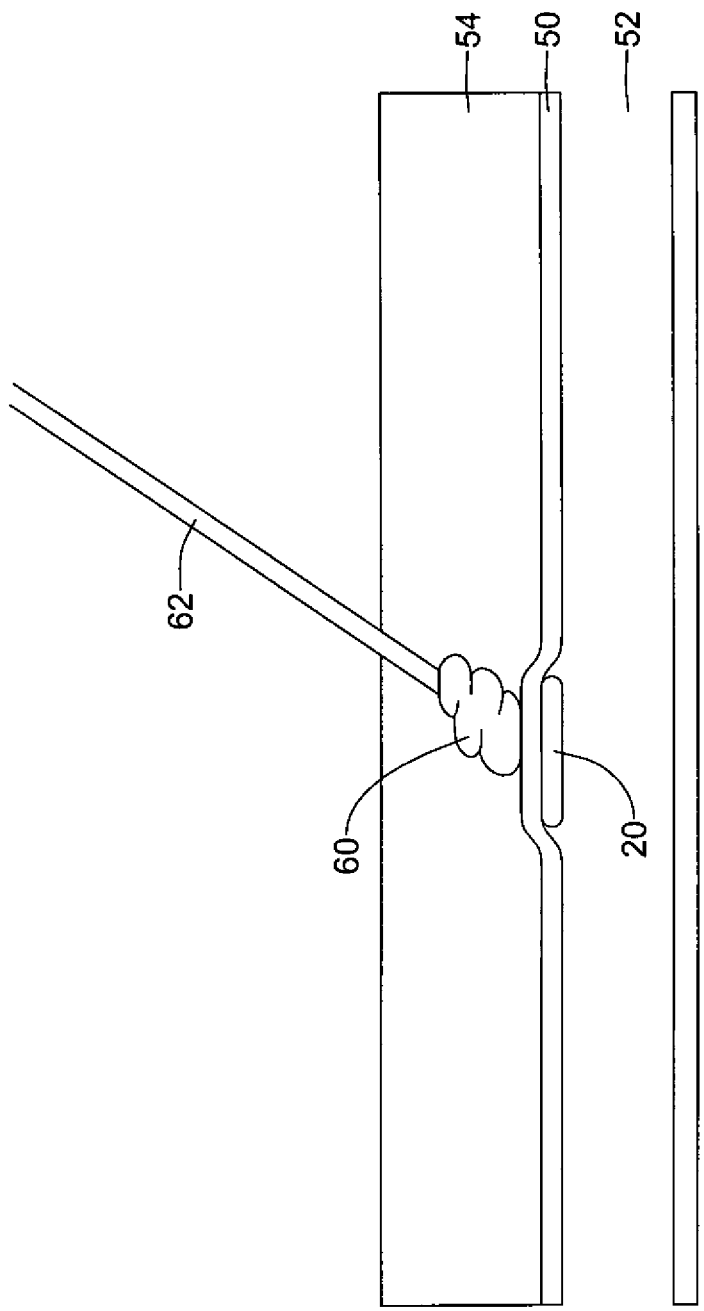
FIG. 3 illustrates an embodiment of the disclosure securing a hemostatic plug before dissolution of the anchor portion.

FIG. 1 illustrates an embodiment of an anchor assembly 10 of the present disclosure in which anchor 20 is attached to conductive element 30. In use, the long axis of anchor 20 is pivoted to align generally with the axis of conductive element 30. In this configuration, the anchor is inserted in to a vessel through a puncture to be sealed. The anchor may be introduced by means known in the art. Such anchors 20 can be introduced through a wound tract adjacent the vessel puncture site using a catheter, cannula, sheath, or the like 62, as illustrated in FIGS. 2 and 3, which has been previously positioned through the puncture as part of the apparatus used in an intravascular interventional or diagnostic procedure. In some applications, the anchor may serve as tapered tip of the introducing instrument.

Once anchor 20 has been introduced into the vessel to be sealed, it is released and allowed to pivot to a position, generally as depicted in FIG. 1, in which the long axis of the anchor is largely perpendicular to the conductive element 30 and parallel to the interior wall of the vessel (not shown) to be sealed. The conductive element 30 is then withdrawn to seat the anchor 20 in contact with the vessel wall at the puncture site. Slight tension may be applied to the conductive element 30 to maintain the anchor in its position adjacent to and at least partially blocking the puncture to be sealed. The anchor 20 and conductive element 30 may then be employed to introduce, position, and/or secure a biodegradable hemostatic plug (not shown) within the wound tract and adjacent to the exterior of the blood vessel at the puncture site.

A hemostatic plug, pledget, or gel may be introduced over the conductive element 30 or may be deposited adjacent thereto. In some embodiments, the combination of anchor 20 and conductive element 30 may form a portion of a positioning system which allows the hemostatic plug 60 to be positioned more accurately because the location of the inner wall of the vessel to be sealed is accurately known relative to the conductive element 30 and attached anchor 20. As is common in the art, the hemostatic plug is then allowed to seal the wound tract, often by swelling upon exposure to bodily fluids and or externally supplied fluids such as saline.

Once the plug 60 has filled the tract and established a firm position, the anchor 20 serves little or no useful purpose and need no longer be present within the vessel where it may at least partially restrict blood flow by extending into the lumen of the vessel. Accordingly, it is often desirable to employ a bioabsorbable anchor 20 or one which is slowly soluble or dispersible in blood and readily metabolized or excreted.

Anchors known in the art may persist within the body for as long as about 60 to 90 days. Some anchors are essentially permanent. On the other hand, other anchors have been provided which dissolve very rapidly and so may cease to be functional before the puncture is properly sealed. Such rapidly dissolving anchors may release undesirably large pieces of themselves into the blood stream. The anchors 20 of the disclosure provide a measure of control over their rate of dissolution or dispersal not found in the art.

In some embodiments, the anchors 20 of the disclosure may be fabricated using a magnesium anchor element (22, 28) which may be subjected to anodic dissolution/disintegration in a controlled manner. Throughout this disclosure, the term "magnesium" will be understood to include alloys containing lesser amounts of other metals. For example, the magnesium anchors of the disclosure may contain up to 9.5% of rare earth metals, zinc, aluminum, iron, silver, or combinations thereof. In some embodiments, the anchor may be fabricated from an alloy having greater amounts of other metallic elements such as $Mg_{60+x}Zn_{35-x}Ca_5$ ($0 \le x \le 7$).

A dissolution current may be supplied to the anchor 20 through a conductive element 30 optionally augmented by conduction through a biodegradable electroactive polymer such as, for example, poly(3,4-ethylenedioxythiophene) and/or copolymers thereof. Other biodegradable electroactive polymers can also be used. By controlling polarity and current using the conductive element 30 and/or the biodegradable electroactive polymer, degradation of the anchor may be either inhibited or accelerated at will. The rate of degradation may be further controlled by altering the structure of the magnesium anchor element 22 and/or by applying coatings to the magnesium anchor element. For example, the magnesium anchor element 22 may be formed from a magnesium foam 28, as illustrated in the cross-sectional view of FIG. 1B along "A"-"A" of FIG. 1, which can result in a greater surface area being exposed to bodily fluid during anodic dissolution and a reduced mass of the anchor 20 to be dissolved. Fabrication methods, such as inkjet printing followed by sintering, suitable for the production of such foams are known and need not be discussed here in detail. At least some of these fabrication methods can be suited for the incorporation of selected materials within the pores of the foams.

In addition to modifying the shape and or form of the magnesium portion of the anchor 20, the anchor element may be provided with one or more coatings. The coatings (24, 26) may provide an occlusive and/or non-conductive layer which can tend to inhibit decomposition or they may include electroactive components which can provide enhanced electrical conductivity between the anchor and a source of current. In addition, the coating or coatings may include additional components such as heteropolyacids, therapeutic agents, chelating agents, or the like. In some embodiments, a coating or coating may include a metal such as iron which, together with the magnesium, forms a galvanic couple capable of providing the current for anodic dissolution of the magnesium anchor.

In some embodiments, a coating 24 may comprise polylactic acid, polyglycolic acid, or copolymers thereof. In other embodiments, the coating 24 may comprise other known biodegradable polymers. In yet other embodiments, the coating 24 may include functional materials dispersed or dissolved within the coating such as the therapeutic agents, chelating agents, or the like mentioned above. For example, porphyrins and/or ethylenediaminetetraacetic acid (EDTA) may be incorporated in one or more coatings associated with the magnesium anchor element (22, 28) to minimize formation of insoluble products such as magnesium hydroxides and/or to accelerate dissolution of the magnesium anchor element (22, 28). Other chelating agents such as citric acid and salts thereof may also be employed. In some embodiments, magnesium oxide and calcium and/or magnesium phosphate may be introduced into one or more coating layers to modulate dissolution of the anchor and/or the release of therapeutic agents such as antithrombotic drugs.

Useful additives for the composite anchors of this disclosure are members of the heteropolyacid group. A heteropolyacid is a class of acids made up of hydrogen and oxygen with certain metals and non-metals. Among the better known members of the class are the Keggin and Dawson structures. For the purposes of this disclosure, the term "heteropolyacid" may also be read to encompass metal organic frameworks. These materials can be very strong acids. Without wishing to be bound by theory, it is believed that these materials may contribute to the dissolution of the magnesium anchor by neutralizing the alkaline products produced during magnesium corrosion. In addition, they may promote hydrolysis of polymers such as polylactic acid and polyglycolic acid which may advantageously be used in these constructions. Heteropolyacids are also said to possess antibacterial properties, to provide mechanical reinforcement, and to dissolve quickly in water and blood thereby contributing additional porosity to the structures into which they are incorporated. For these reasons, heteropolyacids may be employed throughout the construction of the disclosed anchors 20. They may be dispersed within the magnesium foam of the anchor element 28;

be coated as a layer 24 on the magnesium anchor element (22, 28), possibly in conjunction with a metal oxide carrier; be incorporated in a biodegradable polymer 24 coating the magnesium anchor; and/or included in an outer layer 26 such as a biodegradable electroactive polymer.

The conductive element 30, which is connected to anchor 20, may comprise a wire 34. In some embodiments, the wire will also be formed from magnesium. The wire may be surrounded by a biodegradable polymer coating 32 such as polyglycolic acid or the like. This construction allows the wire 34 to provide current for the dissolution of the anchor 20 and additionally may allow the wire subsequently to be dissolved as well. In some embodiments, more than one wire may be attached to the anchor. As discussed above, the biodegradable polymer coating 32 may comprise components such as therapeutic agents, heteropolyacid, biodegradable electroactive polymer, chelating agents, and the like. When such additional components are present, it may be desirable to provide coating 32 as a multilayer coating or to distribute the additional components non-uniformly throughout the thickness of the coating.

In use, a bioabsorbable anchor 20 and conductive element 30 of the disclosure may be introduced into the blood vessel to be sealed by conventional means, e.g., through a catheter, cannula, sheath, or the like, in which the long axis of the anchor 20 is generally aligned with the conductive element 30 and the axis of the insertion device to minimize the cross-sectional area required for the anchor to pass through the puncture in the vessel wall to be sealed.

As illustrated in FIG. 2, once deployed within the lumen 52 defined by the walls 50 of the vessel, the anchor 20 may pivot about a connection to the conductive element 30 to assume an orientation approximately perpendicular to the conductive element as the conductive element is partially withdrawn through the puncture to seat the anchor 20 against the vessel wall 50 at the puncture site.

As illustrated in FIG. 3, hemostatic plug 60 may then be positioned adjacent to the outer wall of the vessel 50 within the overlying tissue 54 and allowed to swell thereby sealing the wound tract. The biodegradable hemostatic plug 60 may be any of those known in the art, such as gelatin or collagen sponges, fibers, and the like. In some embodiments, the biodegradable hemostatic plug 60 may comprise components or coatings such as a bioabsorbable electroactive polymer, a heteropolyacid, therapeutic agents and the like.

When the biodegradable hemostatic plug 60 has sufficiently sealed the wound tract, an electric current may be passed through the anchor 20 and the conductive element 30 to initiate dissolution of the anchor at a rate different from the rate at which the anchor would dissolve in the absence of the electric current. The current may be supplied by a battery or power supply (not shown) external to the body. In some embodiments, the current may be supplied by a galvanic couple within the body. For example, a layer of iron may be deposited on the biodegradable hemostatic plug 60. The iron-magnesium couple may be configured to generate a current which is passed through the conductive element 30 to the anchor 20, possibly with the aid of a biodegradable electroactive polymer at one or more points along the conductive path. Although the current may not directly act upon the coating(s) (24, 26), the relatively thin coatings may dissolve at an accelerated rate when their inner surfaces are exposed by the removal of the magnesium core (22, 28) and/or when other components, such as a heteropolyacid, are released or exposed in the vicinity.

The return path necessary to complete the circuit may be completed in a variety of ways which are within the skill of one in the art. For example, when the current is supplied by an external battery connected to wire 34, the return path may be provided by the patient's bodily fluids and tissues and a conductive skin patch which is connected in turn to the battery. As noted above, the return path for a galvanic couple may be provided within the body through bodily fluids.

In some embodiments, a wire 34 within the conductive element 30 may be dissolved as well. In addition to dissolving the anchor 20 and optionally the conductive element, the current may cause or inhibit migration of components, within any of the coating(s), the conductive element 30, and/or the hemostatic plug 60, such as therapeutic drugs contained therein. In some embodiments, it is believed that outward migration of species contained within the polymeric components will result in the creation of pores having high surface area which further may enhance the rate of dissolution of the polymeric components.

The effectiveness of current in accelerating dissolution of a magnesium plug may be judged by the following data.

TABLE 1

| Weight Loss (milligram) | Time (days) | Current (microampere) |
|---|---|---|
| 6 | 56 | 10 |
| 10 | 18 | 50 |
| 10 | 9.5 | 100 |
| 10 | 2 | 500 |

In some embodiments, the polarity of an applied voltage may initially be reversed to inhibit premature dissolution of the anchor. In other embodiments, current supplied to drive dissolution of the anchor 20 will vary with time to produce a corresponding variation in the rate at which the anchor is dissolved. Accordingly, the rate of dissolution may be tailored to be rapid initially and to slow as the remaining anchor volume decreases. Conversely, the initial rate of dissolution may be slow to insure that the anchor is fully functional as the hemostatic plug engages with the wound tract and initial healing occurs and rapid during the final stages of anchor removal. Similarly, the dissolution of an anchor 20 may be paused during the process or may be driven rapidly to completion if that becomes medically desirable.

Various modifications and alterations of embodiments of the present disclosure will become apparent to those skilled in the art without departing from the scope and principles of this invention, and it should be understood that this invention is not to be unduly limited to the illustrative embodiments set forth hereinabove. Although the illustrative embodiments have related to elongated anchors for vascular sealing devices, it will be appreciated that the inventive principle may be applied to other configurations and other devices. All publications and patents are herein incorporated by reference to the same extent as if each individual publication or patent was specifically and individually indicated to be incorporated by reference.

What is claimed is:

1. A bioabsorbable anchor for a vascular closure device comprising:
    a magnesium anchor;
    a biodegradable polymer coating associated with the magnesium anchor;
    a conductive element connected to the magnesium anchor; and
    a biodegradable electroactive polymer associated with one or more of the magnesium anchor, the biodegradable polymer, and the conductive element.

2. The bioabsorbable anchor of claim 1, wherein the biodegradable electroactive polymer includes poly(3,4-ethylenedioxythiophene).

3. The bioabsorbable anchor of claim 1, wherein the biodegradable polymer coating includes at least one of polylactic acid, polyglycolic acid, or a combination of polylactic acid and polyglycolic acid.

4. The bioabsorbable anchor of claim 1, wherein the biodegradable polymer coating further comprises a heteropolyacid.

5. The bioabsorbable anchor of claim 1, wherein the magnesium anchor comprises magnesium foam.

6. The bioabsorbable anchor of claim 5, wherein the magnesium foam further comprises a heteropolyacid.

7. The bioabsorbable anchor of claim 1, wherein the magnesium anchor is coated with at least one of polylactic acid, polyglycolic acid, or a combination of polylactic acid and polyglycolic acid.

8. The bioabsorbable anchor of claim 7, wherein the coated magnesium anchor is further coated with a heteropolyacid.

9. The bioabsorbable anchor of claim 1, wherein the conductive element connected to the magnesium anchor is coated with a biodegradable polymer.

10. The bioabsorbable anchor of claim 1, wherein the magnesium anchor is connected to a source of electric current.

11. A method of deploying a vascular closure device comprising:
   providing an anchor for a vascular closure device, said anchor further comprising:
   a magnesium anchor member;
   a biodegradable polymer coating associated with the magnesium anchor member;
   a conductive element connected to the magnesium anchor member; and
   a biodegradable electroactive polymer associated with one or more of the magnesium anchor, the biodegradable polymer, and the conductive element;
   disposing the anchor in a blood vessel such that the conductive element extends through a puncture site in a wall of the blood vessel;
   applying tension to the conductive element to seat the anchor against a vessel wall at the puncture site;
   positioning a biodegradable hemostatic plug adjacent to an exterior vessel wall opposite the anchor; and
   passing an electric current through the magnesium anchor member via the conductive element connected to the magnesium anchor member thereby causing the anchor to dissolve at a rate different from the rate at which the anchor would dissolve in the absence of the electric current.

12. The method of claim 11, wherein the biodegradable hemostatic plug comprises a biodegradable electroactive polymer.

13. The method of claim 11, wherein at least one of the biodegradable hemostatic plug, the magnesium anchor member, and the biodegradable polymer coating the magnesium anchor member includes poly(3,4-ethylenedioxythiophene).

14. The method of claim 11, wherein the electric current is supplied from a source outside of a body.

15. The method of claim 11, wherein the electric current is supplied from a source inside of a body.

16. The method of claim 11, wherein the anchor further comprises a heteropolyacid.

17. The method of claim 11, wherein the magnesium anchor member comprises a magnesium foam.

18. A bioabsorbable anchor for vascular closure devices comprising:
   a magnesium anchor;
   a biodegradable polymer coating the magnesium anchor;
   a biodegradable electroactive polymer;
   a heteropolyacid;
   a conductive element connected to the magnesium anchor; and
   a source of electric current connected to the magnesium anchor by the conductive element.

19. The bioabsorbable anchor of claim 18, wherein the magnesium anchor comprises magnesium foam.

20. The bioabsorbable anchor of claim 18, wherein the heteropolyacid is present in at least one of the magnesium anchor, the biodegradable polymer coating, the biodegradable electroactive polymer, and combinations thereof.

* * * * *